US008609420B2

(12) United States Patent
Samuel et al.

(10) Patent No.: US 8,609,420 B2
(45) Date of Patent: Dec. 17, 2013

(54) QUANTUM DOT CARRIER PEPTIDE CONJUGATES SUITABLE FOR IMAGING AND DELIVERY APPLICATIONS IN PLANTS

(75) Inventors: Jayakumar P. Samuel, Carmel, IN (US); Narasimha C. Samboju, Carmel, IN (US); Kerrm Y. Yau, Carmel, IN (US); Gaofeng Lin, Zionsville, IN (US); Steven R. Webb, Westfield, IN (US); Frank Burroughs, Noblesville, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/427,750

(22) Filed: Mar. 22, 2012

(65) Prior Publication Data
US 2012/0244569 A1 Sep. 27, 2012

Related U.S. Application Data

(60) Provisional application No. 61/466,804, filed on Mar. 23, 2011.

(51) Int. Cl.
| | |
|---|---|
| C07K 14/415 | (2006.01) |
| C12N 15/87 | (2006.01) |
| C12N 15/74 | (2006.01) |
| A01H 5/10 | (2006.01) |
| B82Y 10/00 | (2011.01) |
| B82Y 30/00 | (2011.01) |
| B82Y 5/00 | (2011.01) |

(52) U.S. Cl.
USPC ........... 435/468; 435/470; 435/476; 800/293; 800/320.1; 977/728; 977/774; 977/704; 977/705

(58) Field of Classification Search
None
See application file for complete search history.

(56) References Cited

U.S. PATENT DOCUMENTS

| 2006/0251726 A1 | 11/2006 | Lin et al. | |
| 2009/0104700 A1* | 4/2009 | Samuel et al. | ................ 435/412 |
| 2010/0311168 A1 | 12/2010 | Samuel et al. | |

FOREIGN PATENT DOCUMENTS

WO WO2008148223 12/2008

OTHER PUBLICATIONS

Chugh et al. (FEBS Journal 275 (2008), pp. 2403-2414).*
Delehanty, James, et al., "Delivering quantum dot-peptide bioconjugates to the cellular cytosol: escaping from the endolysosmal system," Integrative Biology, May 4, 2010, pp. 265-277, vol. 2.
Liu, Betty R., et al., "Cell-penetrating peptide-functionized Quantum Dots for Intracellular Delivery," Nanosci Nanotechnol, Dec 2010, pp. 7897-7905, vol. 10.
International Search Report and Written Opinion for PCT/US2012/030195, mailed Sep. 26, 2012.
Akerman, M. E., et al, "Nanocrystal targeting in vivo," Proc. Natl. Acad. Sci. U.S.A. 2002, pp. 12617-12621.
Duan, H et al., "Cell-penetrating quantum dots based on multivalent and endosome-disrupting surface coatings," J. Am. Chem. Soc., 2007, pp. 3333-3338, vol. 129.
Delehanty, J. B., et al., "Self-assembled quantum dot-peptide bioconjugates for selective intracellular delivery" Bioconjugate Chem., 2006, pp. 920-927, vol. 17.
Jaiswal, J. K., et al., "Long-term multiple color imaging of live cells using quantum dot bioconjugates," Nat. Biotechnol., 2003, pp. 47-51, vol. 21.
Lagerholm, B. C., et al., "Multicolor coding of cells with cationic peptide coated quantum dots," Nano Lett., 2004, pp. 2019-2022, vol. 4.
Lewin, M., et al., "Tat peptide-derivatized magnetic nanoparticles allow in vivo tracking and recovery of progenitor cells," Nat. Biotechnol. 2002, pp. 410-414, vol. 18.
Mae, M., et al., "Cell-penetrating peptides as vectors for peptide, protein and oligonucleotide delivery," Curr. Opin. Pharmacol. 2006, pp. 509-514, vol. 6.
Pooga, M., et al. "Cellular translocation of proteins by transportan," Faseb J. 2001, pp. 1451-1453, vol. 15.
Ruan, G., et al., "Imaging and tracking of Tat peptide-conjugated quantum dots in living cells: new insights into nanoparticle uptake, intracellular transport, and vesicle shedding," J. Am. Chem. Soc., 2007, pp. 14759-14766, vol. 129.
Smith, A. M., et al., "Chemical analysis and cellular imaging with quantum dots," Analyst 2004, pp. 672-677, vol. 129.
Turner, J. J., "Synthesis, cellular uptake and HIV-1 Tat-dependent trans-activation inhibition activity of oligonucleotide analogues disulphide-conjugated to cell-penetrating peptides," Nucleic Acids Res., 2005, pp. 27-42.
Bendifallah, N., et al., "Evaluation of cell-penetrating peptides (CPPs) as vehicles for intracellular delivery of antisense peptide nucleic acid (PNA)" Bioconjugate Chem., 2006, vol. 17, pp. 750-758.
Snyder, E. L., et al., "Recent advances in the use of protein transduction domains for the delivery of peptides, proteins and nucleic acids in vivo," Expert Opin. Drug Delivery 2005, vol. 2, pp. 43-51.
Watson, A., et al., "Lighting up cells with quantum dots," Biotechniques 34, 2003, pp. 296-298, 300, 302-303.
Heitz, F., et al., "Twenty years of cell-penetrating peptides: from molecular mechanisms to therapeutics," British Journal of Pharmacology, 2009, vol. 157, pp. 195-206.
Barroso, M., "Quantum Dots in Cell Biology," Journal of Histochemistry & Cytochemistry, 59(3), 2011, pp. 237-251.

* cited by examiner

*Primary Examiner* — David T Fox
*Assistant Examiner* — Jared Shapiro
(74) *Attorney, Agent, or Firm* — Ronald S. Maciak; TraskBritt, P.C.

(57) ABSTRACT

Provided are methods for introducing a molecule of interest into a plant cell having a cell wall by using a QD-peptide conjugate having a quantum dot (QD) with one or more cell penetrating peptides (CPPs). Methods are provided for genetically or otherwise modifying plants and for treating or preventing disease in plant cells comprising a cell wall.

18 Claims, 2 Drawing Sheets

QUANTUM DOT CARRIER PEPTIDE CONJUGATES SUITABLE FOR IMAGING AND DELIVERY APPLICATIONS IN PLANTS

CROSS-REFERENCE TO RELATED APPLICATION

This application claims the benefit of U.S. Provisional Patent Application Ser. No. 61/466,804, filed Mar. 23, 2011, the disclosure of which is hereby incorporated herein in its entirety by this reference. The application is also a continuation-in-part of U.S. patent application Ser. No. 12/245,685, to Samuel et al., which claims the benefit of U.S. Provisional Patent Application Ser. No. 60/978,059, for "METHODS FOR TRANSFERRING MOLECULAR SUBSTANCES INTO PLANT CELLS."

TECHNICAL FIELD

The present disclosure generally relates to methods for introducing a molecule of interest into a plant cell having a cell wall by using a QD-peptide conjugate having a quantum dot (QD) with one or more cell penetrating peptides (CPPs).

BACKGROUND OF THE INVENTION

Nanoparticles have unique properties that have been exploited for use in the delivery of DNA to cells. Metal nanoparticles, such as gold (Au) nanoparticles have been used for DNA delivery because of their low cytotoxicity and ease of functionalization with various ligands of biological significance. In addition to metal nanoparticles, semi-conductor nanoparticles (e.g., quantum dots) ("QD") within the size range of 3-5 nm have also been used as carriers to deliver molecules into cells. DNA and proteins can be linked to the ligand attached to the QD surface (see, e.g., F. Patolsky et al., *J. Am. Chem. Soc.* 125, 13918 (2003)).

Nanoparticles have been used to deliver plasmid DNA to a variety of animal cells. It has been found that when DNA coated nanoparticles are incubated with cells not having a cell wall, the cells take up the nanoparticles and begin expressing any genes encoded on the DNA. However, the contemporary plant gene delivery is challenging due to the presence of plant cell walls, which leads to the common reliance on invasive delivery means for genetic transformation of plants. Where nanoparticle-mediated delivery to cells normally having a cell wall is desired, the cell's wall is stripped before the addition of the particles to protoplasts of plant (see, F. Torney et al., *Nature Nanotechnol.* 2 (2007)). In plant cells, the cell wall stands as a barrier for the delivery of exogenously applied molecules. Many invasive methods, like gene gun (biolistics), microinjection, electroporation, and *Agrobacterium*, have been employed to achieve gene and small molecule delivery into these walled plant cells, but delivery of proteins has only been achieved by microinjection. Delivery of small molecules and proteins in the presence of a plant cell wall remains unexplored and would be advantageous in order to develop enabling technologies to be deployed in intact plant cell/tissue or organ for in vitro and in vivo manipulations.

Cell penetrating peptides (CPPs) are a novel and fast growing class of short peptides that are known to play an important role in translocation of a wide range of cargo complexes including proteins and DNA across the bio-membranes in mammalian and human cell lines. J. Schwartz and S. Zhang (2000), Peptide-Mediated Cellular Delivery, *Curr. Opin. Mol. Ther.* 2:162-167; Ü. Langel (2002), Preface in *Cell Penetrating Peptides; Processes and Applications*, Ü. Langel, editor, CRC Press, Boca Raton; E. Vives and B. Lebleu (2002), The Tat-Derived Cell-Penetrating Peptide in *Cell-Penetrating Peptides; Processes and Applications*, Ü. Langel, editor, CRC Press, Boca Raton, pp. 3-22. While CPPs have been shown to facilitate cargo delivery in mammalian cells, the use of CPP in plant cells for transfection studies has been limited by a number of factors. A major obstacle to adapting this technology to plants is that, unlike animal cells, plant cells present a dual barrier system (cell wall and plasma membrane) for the internalization of CPPs and their cargos. Therefore, CPPs must overcome these two barriers for efficient translocation. CPPs have been used in plant cells but typically rely on use of permeabilization agents and techniques with the use of CPPs to effectuate delivery of cargo delivery to the plant cells. The HIV-1 TAT protein transduction domain (PTD) is one of the most well studied translocating peptides. Recent reports have shown the potential of TAT-PTD and its oligomers for plasmid delivery by forming a complex with the negatively charged DNA in mammalian cells. I. Ignatovich, E. Dizhe, A. Pavlotskaya, B. Akifiev, S. Burov, S. Orlov and A. Perevozchikov (2003), Complexes of Plasmid DNA with Basic Domain 47-57 of the HIV-1 Tat Protein Are Transferred to Mammalian Cells by Endocytosis-mediated Pathways, *J. Biol. Chem.* 278:42625-42636; C. Rudolph, C. Plank, J. Lausier, U. Schillinger, R. H. Müller and J. Rosenecker (2003), Oligomers of the Arginine-Rich Motif of the HIV-1 TAT Protein are Capable of Transferring Plasmid DNA into Cells, *J. Biol. Chem.* 278:11411-11418; Z. Siprashvili, F. Scholl, S. Oliver, A. Adams, C. Contag, P. Wender and P. Khavari (2003), Gene Transfer via Reversible Plasmid Condensation with Cysteine-Flanked, Internally Spaced Arginine-Rich Peptides, *Hum. Gene. Ther.* 14 (13):1225-33; I. Hellgren, J. Gorman and C. Sylvén (2004), Factors Controlling the Efficiency of Tat-mediated Plasmid DNA Transfer, *J. Drug. Target.* 12 (1):39-47. Other peptides that have been shown to have translocating properties include pVEC, transportan, penetratin, pep-1 peptides and fragments thereof.

Coating QDs with peptides is one approach that has become popular in the nanoparticle surface engineering for various biotechnological processes. For instance, attachment of cell-penetrating peptides, such as polyarginine and TAT-derived peptides, to the QD surface has allowed translocating QDs into animal cells. Recently, CPPs have become widely used as vehicles for the cellular delivery of molecules in basic and applied biomedical research. With their help, it is possible now to introduce membrane-impermeable substances like peptic nucleic acids (PNA), proteins, oligonucleotides, or nanoparticles into mammalian cells. There is a growing attraction for plant biologists in using CPPs for delivery of biomolecules into the cells and transient expression of the same. Thus, there still remains a need for a method of stable incorporation of genes and other molecules of interest in plants through use of nanoparticle-based delivery.

BRIEF SUMMARY OF THE INVENTION

The following embodiments are described in conjunction with systems, tools and methods which are meant to be exemplary and illustrative, and not limiting in scope.

One embodiment of the invention includes a method of introducing a molecule of interest into a plant cell having a cell wall to effect stable transformation of a plant and seeds. The method includes providing the plant cell having a cell wall and interacting a quantum dot (QD) with one or more cell penetrating peptides (CPPs) to form a QD-peptide conjugate, and attaching one or more molecules of interest to the one or more CPPs to form an activated QD-peptide conjugate. The cell and the activated QD-peptide conjugate are placed in contact with each other, under conditions permitting the uptake of the same into the cell having the cell wall.

Another embodiment of the invention includes a method of stably expressing a gene. The method includes providing a plant cell having a cell wall, interacting a quantum dot (QD) with one or more cell penetrating peptides (CPPs) to form a QD-peptide conjugate, and attaching one or more genes to the one or more CPPs to form an activated QD-peptide conjugate. The plant cell having a cell wall and the activated QD-peptide conjugate are placed in contact with each other, and the QD-peptide conjugate and the one or more genes are placed under conditions permitting the uptake of the same into the plant cell having the cell wall. The gene in the progeny of a plant having the plant cell is then expressed.

Yet another embodiment of the invention includes a method for transferring a molecular substance into a plant cell. The method includes interacting a quantum dot (QD) with one or more cell penetrating peptides (CPPs) to form a QD-peptide conjugate, and interacting the QD-peptide conjugate with a plasmid DNA to form an activated QD-peptide conjugate structure. The activated QD-peptide conjugate structure is placed in contact with an intact wall-bearing plant cell under conditions permitting the uptake of the one or more CPPs and one or more genes from the plasmid DNA into the plant cell.

Another particular embodiment of the invention includes a method of screening and identifying plant transformation. The method includes providing a plant cell having a cell wall, interacting a quantum dot (QD) with one or more cell penetrating peptides (CPPs) to form a QD-peptide conjugate, and attaching one or more molecules of interest to the one or more CPPs to form an activated QD-peptide conjugate. The cell having a cell wall and the activated QD-peptide conjugate are placed in contact with each other, and the QD-peptide conjugate and the molecule of interest are placed under conditions permitting the uptake of the same into the plant cell having the cell wall. The plant cell having the cell wall is then imaged.

In addition to the exemplary aspects and embodiments described above, further aspects and embodiments will become apparent in view of the following descriptions.

DETAILED DESCRIPTION OF THE INVENTION

Figure 1:
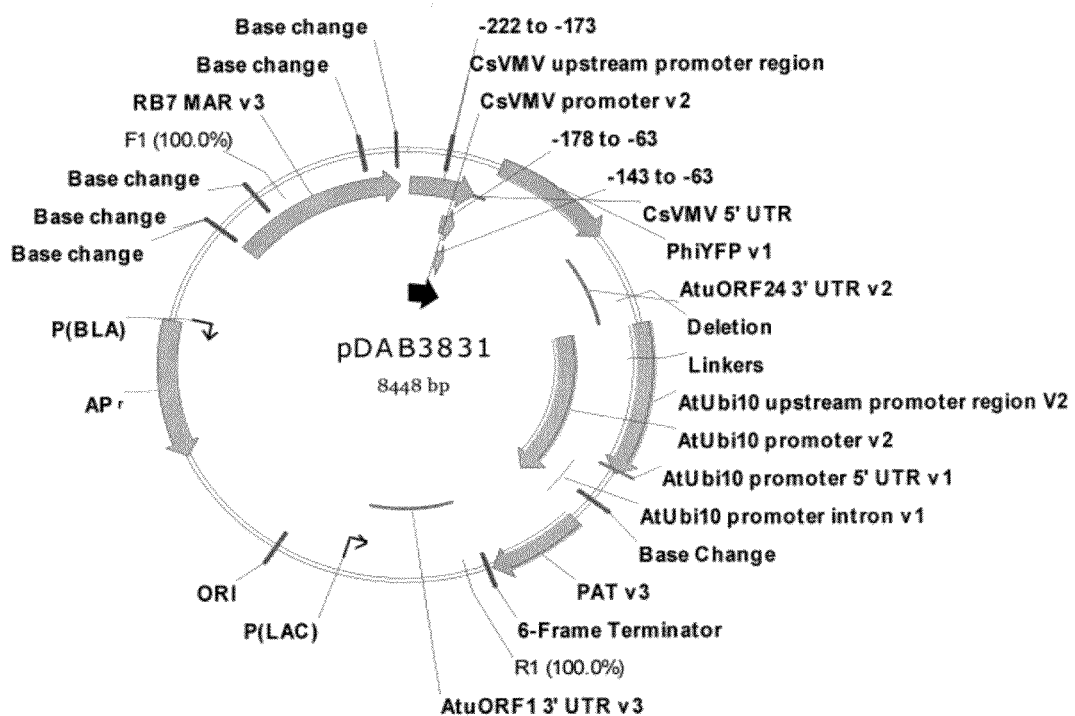
FIG. 1. illustrates a plasmid map of pDAB3831,
FIG. 2. illustrates an embodiment of a quantum dot/peptide conjugate.
Figure 2:
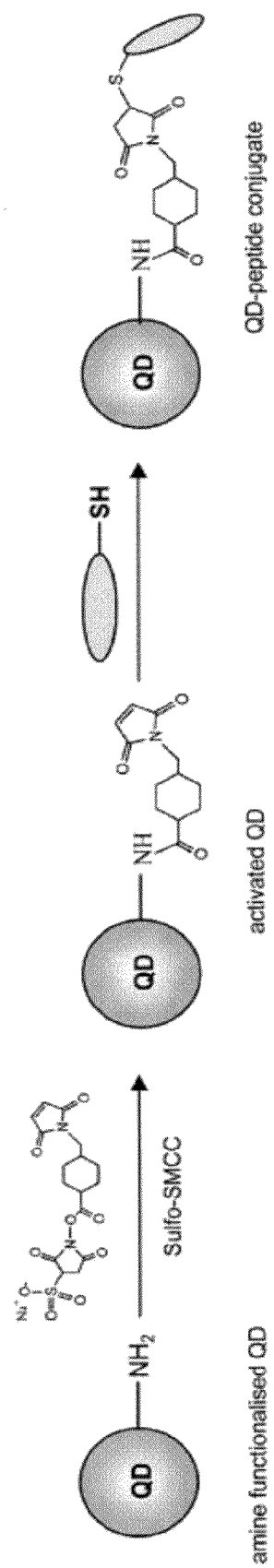

In the description and tables which follow, a number of terms are used. In order to provide a clear and consistent understanding of the specification and claims, including the scope to be given such terms, the following definitions are provided:

Backcrossing. Backcrossing may be a process in which a breeder repeatedly crosses hybrid progeny back to one of the parents, for example, a first generation hybrid $F_1$ with one of the parental genotypes of the $F_1$ hybrid.

Embryo. The embryo may be the small plant contained within a mature seed.

Resistant to an herbicide. Resistance to a dosage of an herbicide refers to the ability of a plant to survive (i.e., the plant may be not killed) by that dosage of herbicide. In some cases, tolerant plants may temporarily yellow or otherwise exhibit some herbicide-induced injury (e.g., excessive tillering and/or growth inhibition), but recover.

Stabilized. Stabilized refers to characteristics of a plant that are reproducibly passed from one generation to the next generation of inbred plants of the same variety.

Uptake. Uptake refers to the translocation of a particle, such as a quantum dots, carrier peptides, cell penetrating peptides, and homing peptides, across a cell wall or a cellular membrane, wherein the translocation does not occur solely as a result of momentum imparted to the particle by something other than the cell into which the particle is being uptaken. Non-limiting examples of devices or methods which cause translocation of a particle across a cell wall or a cell membrane solely as a result of momentum imparted to the particle are biolistic, gene gun, microinjection, and/or impalefection technologies.

In some embodiments of the invention, multiple attachment sites or filling of an "added" or "guest" molecule may be engineered on one or more peptides at various and/or multiple sites. This property can be employed, for example, in specific targeting and editing of molecular sites within cells for areas such as biomimetics, targeted deliveries, for non-genetically modified organism options, and transient transformation options in a variety of tree or vegetable crops for trait and disease resistance options. Embodiments of the invention can also be employed to develop suitable bio-sensors. In addition, artificial chromosomes (ACES) may be employed with the methods of the invention as an alternative to current eukaryotic vectors for precise targeting and homologous recombination options.

Particular embodiments of the invention generally relate to the use of multifunctional fluorescent nanoparticles suitable for the delivery of negatively charged molecules, such as, for example, DNA/RNA. Carrier and cell penetrating peptides (CPPs)/homing peptides (HPs) (collectively referred to herein as "CPPs"), such as R9, TAT, MPG and γ-Zein, were incorporated on the surface of luminescent quantum dots (QDs). QD-peptide conjugates were used for efficient DNA delivery into *Arabidopsis* in planta pathways. QD-peptide bioconjugates exhibited no toxic effects in relation to the *Arabidopsis* floral axes growth and seed set. Several stable T1 transformants were identified and the seedlings were analyzed. The carrier based delivery of DNA and the establishment of stable transformation using QDs were shown in plants. Complex payloads can be engineered with smart options to deliver biomolecules and to be targeted into the cells and cell compartments precisely. In particular embodiments, the use of such autofluorescent QDs can be used for imaging options in plants.

According to certain embodiments of the invention, there may be provided a method of introducing a molecule of interest into a plant cell having a cell wall to effect stable transformation of a plant and seeds. The method includes providing the plant cell having a cell wall and interacting a quantum dot (QD) with one or more cell penetrating peptides (CPPs) to form a QD-peptide conjugate, and attaching one or more molecules of interest to the one or more CPPs to form an activated QD-peptide conjugate. The cell and the activated QD-peptide conjugate are placed in contact with each other, under conditions permitting the uptake of the same into the cell having the cell wall.

In some embodiments, several peptides were covalently coupled to QD nanoparticles and delivered into plant cells. Nanoparticles with R9, γ-Zein and MPG CPPs were successfully delivered into plants to achieve stable transformation of plants. In other embodiments, labeled biomolecule were used to track the fate of the cargo in the cytoplasm. An effective uptake of these QD-peptide-DNA conjugates was achieved and that the complex between the DNA and the QD-peptide conjugate was stable as demonstrated by the stable transformation that is transmitted via seeds and resistant T1 seedlings recovered.

In other aspects, the invention relates to the application of QD "carrier" Peptide-Conjugates as a payload for multifunctionalization options for the smart delivery of biofunctionalized biomolecules (e.g., DNA/RNA and enzyme delivery), imaging, and for various biotechnological diagnostics and sensing functions. The present strategy can offer surface and encapsulation chemistry that is quite adaptable, thus facilitating synthesis of a broad range of molecules with different functionality. Key properties in terms of the potential use of these materials in biomolecules and gene delivery are defined by the high density of terminal groups available in such systems. These contribute to the molecules surface characteristics, offer multiple attachment sites (e.g., for conjugation of signal or targeting moieties), and determine the molecular volume, which is important for the ability to sequester other molecules to this complex. The conjugated carrier peptides simultaneously function for the delivery of both the QD and an attached cargo. Furthermore, by complexing the cargo directly to the carrier peptide, the tradeoffs in the number of attached species on the QD surface can be eliminated. Since negatively charged oligonucleotides are not able to translocate the cell wall/membrane barriers and the cell membrane by themselves, the present invention provides, inter alia, effective delivery systems for DNA integration, gene regulation, and editing strategies.

According to embodiments of the present invention, a plant cell having a cell wall may be any plant cell comprising an intact and whole cell wall. Examples of cells having a cell wall include, but are not limited to, algal, tobacco, carrot, maize, canola, rapeseed, cotton, palm, peanut, soybean, sugarcane, *Oryza* sp., *Arabidopsis* sp., and *Ricinus* sp., preferably tobacco, carrots maize, cotton, canola, soybean and sugarcane; more preferably tobacco and carrots. Embodiments of the invention may include cells comprising a cell wall from any tissue or wherever they are found, including but not limited to, in embryos, meristematic cells, callus, pollen, leaves, anthers, roots, root tips, flowers, seeds, pods, stems, and tissue culture.

In embodiments of the invention, a molecule of interest may be any molecule that can be delivered to a plant cell according to the present invention. Molecules of interest, or components of molecules of interest, may comprise, but are not limited to, nucleic acids, DNA, RNA, RNAi molecules, genes, plasmids, cosmids, YACs, BACs, Plant Artificial Chromosomes, Plant Mini-chromosomes, Plant Engineered Trait Loci DNA; polypeptides, enzymes, hormones, glyco-peptides, sugars, fats, signaling peptides, antibodies, vitamins, messengers, second messengers, amino acids, cAMP, drugs, herbicides, fungicides, antibiotics, and/or combinations thereof.

Embodiments of the invention include methods for the prevention or treatment of disease. Non-limiting example embodiments include the delivery of fungicides, antibiotics, and/or other drugs to cells in need thereof using methods of the present invention.

In aspects of the invention, the QD-peptide conjugate may be uptaken into various parts of cells. Examples of locations that the QD-peptide conjugate may be uptaken into include, but are not limited to, cytosol, nucleus, tonoplasts, plastids, etioplasts, chromoplasts, leucoplasts, elaioplasts, proteinoplasts, amyloplasts, chloroplasts, and the lumen of a double membrane. In other embodiments of the invention, the QD-peptide conjugate may be uptake into a cell comprising a cell wall may occur via the symplastic or apoplastic pathway.

Additional embodiments of the invention include genetically modified plant cells and methods for generating them, wherein the plant cells have one or more nucleic acids introduced therein via methods of the present invention. In one example of an embodiment, a plasmid comprising a gene of interest and a selectable marker may be in introduced into a plant cell having a cell well via a QD-peptide conjugate according to the present invention. In further embodiments, stable transformants may be selected that have stably integrated the gene of interest and/or the selectable marker. In alternative embodiments, a plant cell now comprising the gene of interest may be propagated to produce other cells comprising a molecule of interest. In other embodiments, plant cells now comprising a molecule of interest may be a regenerable cell that may be used to regenerate a whole plant including the molecule of interest.

In another aspect, the present invention provides methods of creating regenerable plant cells comprising a molecule of interest for use in tissue culture. The tissue culture will preferably be capable of regenerating plants having substantially the same genotype as the regenerable cells. The regenerable cells in such tissue cultures can be embryos, protoplasts, meristematic cells, callus, pollen, leaves, anthers, roots, root tips, flowers, seeds, pods or stems. Still further, an embodiment of the invention provides plants regenerated from the tissue cultures of the invention.

Alternatively, the present invention provides a method of introducing a desired trait into a plant cell having a cell wall, wherein the method comprises: placing a QD-peptide conjugate and a molecule of interest capable of providing the desired trait to the plant cell in contact with the cell and allowing uptake of the QD-peptide conjugate across the cell wall. Examples of desired traits include, but are not limited to, traits selected from male sterility, herbicide resistance, insect resistance, and resistance to bacterial disease, fungal disease, and/or viral disease.

Further aspects of the invention provide for the methods of generating of stabilized plant lines comprising a desired trait or molecule of interest, wherein the desired trait or molecule of interest may be first introduced by uptake of a QD-peptide conjugate across a plant cell wall. Methods of generating stabilized plant lines are well known to one of ordinary skill in the art and may include techniques such as, but not limited to, selfing, backcrosses, hybrid production, crosses to populations, and the like. All plants and plant cells comprising a desired trait or molecule of interest first introduced into the plant cell (or its predecessors) by uptake of a QD-peptide conjugate across a cell wall are within the scope of this invention. Advantageously, the plant cells comprising a desired trait or molecule of interest first introduced into the plant or cell (or its predecessors) by uptake of a QD-peptide conjugate across a cell wall can be used in crosses with other, different, plant cells to produce first generation ($F_1$) hybrid cells, seeds, and/or plants with superior characteristics.

In embodiments wherein the molecule of interest comprises one or more gene(s), the gene(s) may be a dominant or recessive allele. By way of example, the gene(s) will confer such traits as herbicide resistance, insect resistance, resistance for bacterial resistance, fungal resistance, viral disease resistance, male fertility, male sterility, enhanced nutritional quality, and industrial usage.

With the advent of molecular biological techniques that have allowed the isolation and characterization of genes that encode specific protein or RNA products (e.g., RNAi), scientists in the field of plant biology developed a strong interest in engineering the genome of cells to contain and express foreign genes, or additional or modified versions of native or endogenous genes (perhaps driven by different promoters) in order to alter the traits of a cell in a specific manner. Such foreign additional and/or modified genes are referred to herein collectively as "transgenes." Over the last fifteen to twenty years, several methods for producing transgenic cells have been developed and, in particular embodiments, the present invention relates to transformed versions of cells and methods of producing them via introducing into a cell having a cell wall a transgene via uptake of a QD-peptide conjugate across a cell wall. In embodiments of the invention, the transgene may be contained in an expression vector.

Cell transformation may involve the construction of an expression vector which will function in a particular cell. Such a vector may comprise DNA that includes a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed cells using transformation methods as described herein to incorporate transgene(s) into the genetic material of a plant cell comprising a cell wall.

Use of QD-peptide conjugates according to methods of the present invention has produced stably transformed plants and demonstrated the expression of the stably transformed herbicide gene with the phenotype where high herbicide tolerance was rendered into the transgenic T1 plant. This plant was shown to be fertile as it produced T2 seeds.

Expression Vectors for Uptake Via QD-Peptide Conjugate: Marker Genes

Expression vectors may include at least one genetic marker, operably linked to a regulatory element (a promoter, for example) that allows transformed cells containing the marker to be either recovered by negative selection (i.e., inhibiting growth of cells that do not contain the selectable marker gene) or by positive selection (i.e., screening for the product encoded by the genetic marker). Many selectable marker genes for transformation are well known in the transformation arts and include, for example, genes that code for enzymes that metabolically detoxify a selective chemical agent which may be an antibiotic or an herbicide, or genes that encode an altered target which may be insensitive to the inhibitor. A few positive selection methods are also known in the art.

One commonly used selectable marker gene suitable for plant transformation may include the neomycin phosphotransferase II (nptII) gene under the control of plant regulatory signals, which confers resistance to kanamycin. See, e.g., Fraley et al., *Proc. Natl. Acad. Sci. U.S.A.* 80:4803 (1983). Another commonly used selectable marker gene may be the hygromycin phosphotransferase gene, which confers resistance to the antibiotic hygromycin. See, e.g., Vanden Elzen et al., *Plant Mol. Biol.* 5:299 (1985).

Additional selectable marker genes of bacterial origin that confer resistance to antibiotics include gentamycin acetyl transferase, streptomycin phosphotransferase, aminoglycoside-3'-adenyl transferase, and the bleomycin resistance determinant. See Hayford et al., *Plant Physiol.* 86:1216 (1988); Jones et al., *Mol. Gen. Genet.* 210:86 (1987); Svab et al., *Plant Mol. Biol.* 14:197 (1990); Hille et al., *Plant Mol. Biol.* 7:171 (1986). Other selectable marker genes confer resistance to herbicides such as glyphosate, glufosinate or bromoxynil. See Comai et al., *Nature* 317:741-744 (1985); Gordon-Kamm et al., *Plant Cell* 2:603-618 (1990); and Stalker et al., *Science* 242:419-423 (1988).

Other selectable marker genes suitable for plant transformation are not of bacterial origin. These genes include, for example, mouse dihydrofolate reductase, plant 5-enolpyruvylshikimate-3-phosphate synthase and plant acetolactate synthase. See Eichholtz et al., *Somatic Cell Mol. Genet.* 13:67 (1987); Shah et al., *Science* 233:478 (1986); Charest et al., *Plant Cell Rep.* 8:643 (1990).

Another class of marker genes suitable for plant transformation requires screening of presumptively transformed plant cells rather than direct genetic selection of transformed cells for resistance to a toxic substance, such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening transformed cells include β-glucuronidase (GUS), β-galactosidase, luciferase and chloramphenicol acetyltransferase. See R. A. Jefferson, *Plant Mol. Biol. Rep.* 5:387 (1987); Teeri et al., *EMBO J.* 8:343 (1989); Koncz et al., *Proc. Natl. Acad. Sci. U.S.A.* 84:131 (1987), DeBlock et al., *EMBO J.* 3:1681 (1984).

Recently, in vivo methods for visualizing GUS activity that do not require destruction of plant tissue have been made available. Molecular Probes publication 2908, *Imagene Green*™, p. 1-4 (1993) and Naleway et al., *J. Cell Biol.* 115:151a (1991). However, these in vivo methods for visualizing GUS activity have not proven useful for recovery of transformed cells because of low sensitivity, high fluorescent backgrounds, and limitations associated with the use of luciferase genes as selectable markers.

More recently, genes encoding Fluorescent Proteins (e.g., GFP, EGFP, EBFP, ECFP, and YFP) have been utilized as markers for gene expression in prokaryotic and eukaryotic cells. See Chalfie et al., *Science* 263:802 (1994). Fluorescent proteins and mutations of fluorescent proteins may be used as screenable markers.

Expression Vectors for Uptake Via QD-Peptide Conjugates: Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA that may be upstream from the start of transcription and that may be involved in recognition and binding of RNA polymerase and other proteins to initiate transcription. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific." A "cell type" specific promoter primarily drives expression in certain cell types in one or more organs, for example, vascular cells in roots or leaves. An "inducible" promoter may be a promoter which may be under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter may be a promoter which may be active under most environmental conditions.

A. Inducible Promoters

An inducible promoter may be operably linked to a gene for expression in a cell. Optionally, the inducible promoter may be operably linked to a nucleotide sequence encoding a signal sequence which may be operably linked to a gene for expression in a cell. With an inducible promoter, the rate of transcription increases in response to an inducing agent.

Any inducible promoter can be used in the instant invention. See Ward et al., Plant Mol. Biol. 22:361-366 (1993). Exemplary inducible promoters include, but are not limited to: those from the ACEI system that responds to copper (Mett et al., *PNAS* 90:4567-4571 (1993)); In2 gene from maize that responds to benzenesulfonamide herbicide safeners (Hershey et al., *Mol. Gen. Genetics* 227:229-237 (1991); and Gatz et al., *Mol. Gen. Genetics* 243:32-38 (1994)); and Tet repressor from Tn10 (Gatz et al., *Mol. Gen. Genetics* 227:229-237 (1991)). A particularly useful inducible promoter may be a promoter that responds to an inducing agent to which plants do not normally respond. An exemplary inducible promoter may be the inducible promoter from a steroid hormone gene, the transcriptional activity of which may be induced by a glucocorticosteroid hormone. Schena et al., *Proc. Natl. Acad. Sci. U.S.A.* 88:0421 (1991).

B. Constitutive Promoters

A constitutive promoter may be operably linked to a gene for expression in a cell or the constitutive promoter may be operably linked to a nucleotide sequence encoding a signal sequence which may be operably linked to a gene for expression in a cell.

Different constitutive promoters can be utilized in the instant invention. Exemplary constitutive promoters include, but are not limited to: promoters from plant viruses, such as the 35S promoter from CaMV (Odell et al., *Nature* 313:810-812 (1985)); promoters from rice actin genes (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); and maize H3 histone (Lepetit et al., *Mol. Gen. Genetics* 231:276-285 (1992) and Atanassova et al., *Plant Journal* 2 (3): 291-300 (1992)). The ALS promoter, XbaI/NcoI fragment 5' to the *Brassica napus* ALS3 structural gene (or a nucleotide sequence similarity to said XbaI/NcoI fragment), represents a particularly useful constitutive promoter. See PCT application WO 96/30530.

C. Tissue-Specific or Tissue-Preferred Promoters

A tissue-specific promoter may be operably linked to a gene for expression in a cell. Optionally, the tissue-specific promoter may be operably linked to a nucleotide sequence encoding a signal sequence which may be operably linked to a gene for expression in a cell. Plants transformed with a gene of interest operably linked to a tissue-specific promoter can produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter—such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11): 2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm 13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Transport of protein produced by transgenes to a subcellular compartment, such as the chloroplast, vacuole, peroxisome, glyoxysome, cell wall or mitochondrion or for secretion into the apoplast, can be accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein may be ultimately compartmentalized. Alternatively such subcellular compartment targeting proteins can be directly linked to a QD-peptide conjugate to direct the QD-peptide conjugate coated with the molecule of interest to the desired subcellular compartment.

The presence of a signal sequence directs a polypeptide to either an intracellular organelle or subcellular compartment, or for secretion to the apoplast. Many signal sequences are known in the art. See, e.g., Becker et al., *Plant Mol. Biol.* 20:49 (1992); P. S. Close, Master's Thesis, Iowa State University (1993); C. Knox et al., "Structure and Organization of Two Divergent Alpha-Amylase Genes from Barley," *Plant Mol. Biol.* 9:3-17 (1987); Lerner et al., *Plant Physiol.* 91:124-129 (1989); Fontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., A short amino acid sequence able to specify nuclear location, *Cell* 39:499-509 (1984); Steifel, et al., Expression of a maize cell wall hydroxyproline-rich glycoprotein gene in early leaf and root vascular differentiation, *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

In aspects of the invention, the transgenic plant provided for commercial production of foreign protein may be a cell or a plant. In other aspects, the biomass of interest may be seed. For the relatively small number of transgenic plants that show higher levels of expression, a genetic map can be generated primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology* CRC Press, Boca Raton 269:284 (1993). Map information concerning chromosomal location may be useful for proprietary protection of a subject transgenic plant. If unauthorized propagation may be undertaken and crosses made with other germplasm, the map of the integration region can be compared to similar maps for suspect plants to determine if the latter have a common parentage with the subject plant. Map comparisons would involve hybridizations, RFLP, PCR, SSR and sequencing, all of which are conventional techniques.

Likewise, agronomic genes can be expressed in transformed cells or their progeny. More particularly, plants can be genetically engineered via the methods of the invention to express various phenotypes of agronomic interest. Exemplary genes that may be used in this regard include, but are not limited to, those categorized below.

1. Genes that Confer Resistance to Pests or Disease and that Encode:

A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance genes to engineer plants that are resistant to specific pathogen strains. See, e.g., Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (*Arabidopsis* may be RSP2 gene for resistance to *Pseudomonas syringae*).

B) A gene conferring resistance to a pest, such as soybean cyst nematode. See, e.g., PCT Application WO 96/30517; PCT Application WO 93/19181.

C) A *Bacillus thuringiensis* protein, a derivative thereof or a synthetic polypeptide modeled thereon. See, e.g., Geiser et al., *Gene* 48:109 (1986), which discloses the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D) A lectin. See, for example, the disclosure by Van Damme et al., *Plant Molec. Biol.* 24:25 (1994), who disclose the nucleotide sequences of several *Clivia miniata* mannose-binding lectin genes.

E) A vitamin-binding protein, such as avidin. See PCT application US93/06487. The application teaches the use of avidin and avidin homologues as larvicides against insect pests.

F) An enzyme inhibitor, for example, a protease or proteinase inhibitor or an amylase inhibitor. See, e.g., Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* .alpha.-amylase inhibitor) and U.S. Pat. No. 5,494,813 (Hepher and Atkinson, issued Feb. 27, 1996).

G) An insect-specific hormone or pheromone such as an ecdysteroid or juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H) An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin may be identified in *Diploptera puntata*). See also U.S. Pat. No. 5,266,317 to Tomalski et al., which discloses genes encoding insect-specific, paralytic neurotoxins.

I) An insect-specific venom produced in nature by a snake, a wasp, or any other organism. For example, see Pang et al., *Gene* 116:165 (1992), for disclosure of heterologous expression in plants of a gene coding for a scorpion insectotoxic peptide.

J) An enzyme responsible for a hyperaccumulation of a monoterpene, a sesquiterpene, a steroid, hydroxamic acid, a phenylpropanoid derivative or another non-protein molecule with insecticidal activity.

K) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene.

L) A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

M) A hydrophobic moment peptide. See PCT application WO 95/16776 (disclosure of peptide derivatives of Tachyplesin, which inhibit fungal plant pathogens) and PCT application WO 95/18855 (teaches synthetic antimicrobial peptides that confer disease resistance).

N) A membrane permease, a channel former or a channel blocker. For example, see the disclosure of Jaynes et al., *Plant Sci.* 89:43 (1993), of heterologous expression of a cecropin-β lytic peptide analog to render transgenic tobacco plants resistant to *Pseudomonas solanacearum*.

O) A viral-invasive protein or a complex toxin derived therefrom. For example, the accumulation of viral coat proteins in transformed plant cells imparts resistance to viral infection and/or disease development effected by the virus from which the coat protein gene may be derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

P) An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q) A virus-specific antibody. See, for example, Tavladoraki et al., *Nature* 366:469 (1993), who show that transgenic plants expressing recombinant antibody genes are protected from virus attack.

R) A developmental-arrestive protein produced in nature by a pathogen or a parasite. For example, fungal endo α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein may be described by Toubart et al., *Plant J.* 2:367 (1992).

S) A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

2. Genes that Confer Resistance to an Herbicide:

A) An herbicide that inhibits the growing point or meristem, such as an imidazolinone, sulfonamide, or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B) Glyphosate (resistance conferred by, e.g., mutant 5-enolpyruvylshikimate-3-phosphate synthase (EPSPs) genes (via the introduction of recombinant nucleic acids and/or various forms of in vivo mutagenesis of native EPSPs genes), aroA genes and glyphosate acetyl transferase (GAT) genes, respectively), other phosphono compounds such as glufosinate (phosphinothricin acetyl transferase (PAT) genes from *Streptomyces* species, including *Streptomyces hygroscopicus* and *Streptomyces viridichromogenes*), and pyridinoxy or phenoxy proprionic acids and cyclohexones (AC-Case inhibitor-encoding genes). See, for example, U.S. Pat. No. 4,940,835 to Shah, et al., and U.S. Pat. No. 6,248,876 to Barry et al., which disclose nucleotide sequences of forms of EPSPs which can confer glyphosate resistance to a plant. A DNA molecule encoding a mutant aroA gene can be obtained under ATCC accession number 39256, and the nucleotide sequence of the mutant gene may be disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene may be provided in European application No. 0 242 246 to Leemans et al., DeGreef et al., *Bio/Technology* 7:61 (1989), describe the production of transgenic plants that express chimeric bar genes coding for PAT activity. Exemplary of genes conferring resistance to phenoxy proprionic acids and cyclohexones, such as sethoxydim and haloxyfop include the Acc1-S1, Acc1-S2 and Acc1-S3 genes described by Marshall et al., *Theor. Appl. Genet.* 83:435 (1992). GAT genes capable of conferring glyphosate resistance are described in WO 2005012515 to Castle et al. Genes conferring resistance to 2,4-D, phenoxyproprionic acid and pyridyloxy auxin herbicides are described in WO 2005107437 assigned to Dow AgroSciences LLC.

C) An herbicide that inhibits photosynthesis, such as a triazine (psbA and gs+ genes) or a benzonitrile (nitrilase gene). Przibila et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase may be described by Hayes et al., *Biochem. J.* 285:173 (1992).

3. Genes that Confer or Contribute to a Value-Added Trait, Such as:

A) Modified fatty acid metabolism, for example, by transforming a plant with an antisense gene of stearyl-ACP desaturase to increase stearic acid content of the plant. See Knultzon et al., *Proc. Natl. Acad. Sci. U.S.A.* 89:2624 (1992).

B) Decreased phytate content-1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. In maize for example, this could be accomplished by cloning and then reintroducing DNA associated with the single allele which may be responsible for maize mutants characterized by low levels of phytic acid. See Raboy et al., *Maydica* 35:383 (1990).

C) Modified carbohydrate composition effected, for example, by transforming plants with a gene coding for an enzyme that alters the branching pattern of starch. See Shiroza et al., *J. Bacteol.* 170:810 (1988) (nucleotide sequence of *Streptococcus* mutants fructosyltransferase gene), Steinmetz et al., *Mol. Gen. Genet.* 20:220 (1985) (nucleotide sequence of *Bacillus subtilis* may be levansucrase gene), Pen et al., *Bio/Technology* 10:292 (1992) (production of transgenic plants that express *Bacillus* licheniform may be α-amylase), Elliot et al., *Plant Molec. Biol.* 21:515 (1993) (nucleotide sequences of tomato invertase genes), Sogaard et al., *J. Biol. Chem.* 268:22480 (1993) (site-directed mutagenes may be of barley α-amylase gene), and Fisher et al., *Plant Physiol.* 102:1045 (1993) (maize endosperm starch branching enzyme II).

EXAMPLES

The present invention is further described in the following examples, which are offered by way of illustration and are not intended to limit the invention in any manner.

Example 1

Synthesis of Peptides

The following Cell Penetrating Peptide (CPP) sequences; R9 (Futaki et al., 2001, Suzuki, et al., 2002), MPG (Morris, 1997 and Morris, 1999), and γ-ZEIN (Kogan et al., 2001 and 2002) are listed in Table 1. These peptides were synthesized by the American Peptide Company (Sunnyvale, Calif.) as C-terminal amides. The integrity of the samples was tested using Mass Spectrophotometer using art recognized protocols.

TABLE 1

Amino Acid Sequences and Molecular Masses of the Synthesized Peptides

| | SEQ ID NO: | Peptide | Sequence | Molecular Wt (gm/mole) |
|---|---|---|---|---|
| 1 | SEQ ID NO: 1 | R9 | RRRRRRRRR | 14.23 |
| 2 | SEQ ID NO: 2 | MPG | GALFLGFLGAAGSTMGAWSQPKKKRKV | 28.07 |
| 3 | SEQ ID NO: 3 | γ-ZEIN | (VRLPPP)$_3$ | 19.98 |

Preparation of Quantum Dot—Peptide Conjugates

Quantum dot (QD) and CPP conjugates were produced. Amine-functionalized quantum dots, purchased from EvidentTech (Troy, N.Y.), were activated by adding approximately 1 mg of sulfo-SMCC to 200 μl of amine quantum dots (QD514; n=2.3 nmol) in 200 μl of 50 mM sodium phosphate pH 7.4. CPPs were independently mixed with the maleimide-activated quantum dot in conjugation buffer (1 mM EDTA, 0.1 M phosphate, 0.15 M NaCl, pH 7.2) and incubated at 4° C. overnight. After conjugation, the QD-CPP conjugates were centrifuged at 90,000 rpm for 3 hours, and the pellet was dissolved in a PBS (Phosphate Buffered Saline) solution. QD-CPP conjugates with a QD to CPP molar ratio of 1:100 up to 1:300 were prepared.

Cell Penetrating Peptide-Mediated DNA Delivery on QD Cargo

Plasmid DNA, pDAB3831 (FIG. 1) was complexed with the QD-CPP conjugate. Prior to complexing the DNA with the QD-CPP conjugate, the plasmid DNA was denatured and allowed to re-anneal. This was completed by diluting the DNA to a final volume of 10 μl in DNase-free water. The solution was denatured by heating the solution to 70° C. for 5 minutes and then allowing the solution to slowly cool down to room temperature. The DNA was then complexed with the QD-CPP conjugate at final concentrations of 1:100 CPP-DNA to QD. The QD-CPP-DNA complexation was carried out for 1 hour at 37° C. Finally, sterile 3% sucrose was added until a final volume of 10 ml was achieved. The QD-CPP-DNA complex solution was used to transform the flower buds of *Arabidopsis thaliana*.

Transformation of *Arabidopsis thaliana* with QD-CPP-DNA Complex

Plant Material for in Planta Transformation

Synchronized germination of the seed is important to ensure the uniformity of floral development in the T0 plants. Seed from *Arabidopsis thaliana* cv. Columbia was suspended in 0.1% agar solution and incubated at 4° C. for 48 hours to complete stratification. 60 mg of seed was weighed and transferred to a 15 ml tube. 13 ml of 0.1% agar solution was added and was vortexed until seed was evenly dispersed. This makes a concentration of 4.6 mg seed/1 ml solution (or about 230 seeds/ml). 6 tubes (72 ml solution) were prepared to sow 4 flats that contain 18 (3½-inch) pots in each tray. The seed was incubated at 4° C. for 48 hours to complete stratification. Each pot was sown individually at 1.0 ml of stratified seed per pot. When all the pots were sown, propagation domes were placed on the trays to keep the soil moist. The domes were removed 5 days after the sow date. Seeds were germinated and plants were grown in a Conviron (models CMP4030 and CMP3244, Controlled Environments Limited, Winnipeg, Manitoba, Canada) under long day conditions (16 hours light/8 hours dark) at a light intensity of 120-150 mmol/m$^2$sec under constant temperature (22° C.) and humidity (40-50%). Plants were watered 10 to 14 days after sowing the plants with Hoagland's solution and subsequently with DI water to keep the soil moist but not wet. After 4 weeks post-sow date the flowers were cut back to produce a more even growth of secondary flowers. In the 5th week post-sowing the plants were prepared for the transformation process.

In Planta Transformation and Screening $T_1$ Resistant Plants:

Transformation of *Arabidopsis thaliana* cv. Columbia was completed using a modified protocol from Clough and Bent (S. J. Clough and A. F. Bent, 1998, *Plant J.* 16:735-43). A 10 ml suspension was made with the QD-CPP-DNA solution and used for treatments of the *Arabidopsis* plants (mostly immature flower clusters with some fertilized siliques). Before dipping plants, Silwet L-77 to a concentration of 0.05% (250 ul/500 ml)-0.005% was added to the QD-CPP-DNA solution and mixed well. Above-ground parts of plant were dipped in QD-CPP-DNA solution for 2 to 30 seconds, with gentle agitation. Treated plants were kept under a plastic dome cover for 16 to 24 hours at 22-24° C. The plants were transferred to the Convirons and allowed to grow to maturity and to collect seeds. Selection trays (10.5"×21"×1" trays) were used to screen bulk harvest seed from $T_0$ plants, approximately 10,000 seeds on each tray. Two controls were used to ensure selection spraying was done correctly, Col-0 negative transformation control and Columbia homozygous seed for PAT (phospinothricin acetyl transferase) selectable marker as a positive transformation control. To achieve synchronization seeds were stratified in a 0.1% agar solution for 48 hours prior to sowing. To provide 10,000 seeds per selection tray, 200 mg of seeds were added to a 0.1% agar solution and vortexed until the seeds were evenly distributed. The stratified seeds were then sowed on selection trays filled with Sunshine mix LP5 and sub-irrigated with Hoagland's solution. For the selection spray to be effective it is important that the 40 ml of suspended seed is sown evenly onto the selection tray. After sowing propagation domes were placed on each selection tray and plants were grown for selection. Propagation domes were removed approximately 5 days post-sowing.

In addition, a control experiment was completed. In this experiment a solution containing only DNA, non-complexed to the QD-CPP conjugate, was used to transform *Arabidopsis thaliana*. The protocol above was used for transformation of the DNA alone as a control.

Selection of Transformed Plants

Freshly harvested $T_1$ seed was allowed to dry for 7 days at room temperature. $T_1$ seed was sown in 26.5×51-cm germination trays, each receiving a 200 mg aliquots of stratified $T_1$ seed (~10,000 seed) that had previously been suspended in 40 ml of 0.1% agarose solution and stored at 4° C. for 2 days to complete dormancy requirements and ensure synchronous seed germination.

Sunshine Mix LP5 was covered with fine vermiculite and subirrigated with Hoagland's solution until wet, then allowed to gravity drain. Each 40 ml aliquot of stratified seed was sown evenly onto the vermiculite with a pipette and covered with humidity domes for 4-5 days. Domes were removed 1 day prior to initial transformant selection using glufosinate post-emergence spray.

Seven days after planting (DAP) $T_1$ plants (cotyledon and 2-4-1f stage, respectively) were sprayed five times within five days with a 0.2% solution of Liberty herbicide (200 g ae/L glufosinate, Bayer Crop Sciences, Kansas City, Mo.) at a spray volume of 10 ml/tray (703 L/ha) using a DeVilbiss compressed air spray tip to deliver an effective rate of 280 g ae/ha glufosinate per application. Survivors (plants actively growing) were identified 4-7 days after the final spraying and transplanted individually into 3-inch pots prepared with potting media (Metro Mix 360). Transplanted plants were covered with humidity domes for 3-4 days and placed in a 22° C. growth chamber as before or moved to directly to the greenhouse. Domes were subsequently removed and plants reared in the greenhouse (22±5° C., 50±30% RH, 14 hours light: 10 hours dark, minimum 500 μE/m$^2$s$^1$ natural+supplemental light).

Molecular Analyses

Genomic DNA from *Arabidopsis* transgenic plants was extracted from total leaf material of 6-week-old plants using the Plant DNAZOL kit (Invitrogen, Carlsbad, Calif.) according to the manufacturer's instructions. PCR primers were designed for detection of the yfp and pat transgenes. The yfp primers are presented as SEQ ID NO:4 and SEQ ID NO:5. The pat primers are presented as SEQ ID NO:6 and SEQ ID NO:7.

```
                                         SEQ ID NO: 4
5'-TGTTCCACGGCAAGATCCCCTACG-3'

SEQ ID NO: 5
5'-TATTCATCTGGGTGTGATCGGCCA-3'

SEQ ID NO: 6
5'-GGAGAGGAGACCAGTTGAGATTAG-3'

SEQ ID NO: 7
5'-AGATCTGGGTAACTGGCCTAACTG-3'
```

PCR amplification reactions for pat and yfp were completed using the TaKaRa ExTaq kit (Takara, Otsu, Shiga, Japan). Gene products were amplified in a total reaction volume of 50 μl. The PCR reaction contained 100 ng genomic DNA template, 1×ExTaq reaction buffer, 0.2 mM dNTP, 10 pMol of each primer, and 0.025 units/μL ExTaq. The following PCR conditions were used: 1 cycle at 96° C. for 5 min and 31 cycles of the following conditions 94° C. for 15 s, 65° C. for 30 s, 72° C. for 1 min and a final extension of 72° C. for 7 min. PCR amplification product was analyzed by 0.8% TAE agarose gel electrophoresis and visualized by ethidium bromide staining. Table 2 presents the results of the amplification products that were obtained from these reactions.

TABLE 2

PCR Results for QD Based Carrier Conjugates Used in this Experiment Where Only Representative Samples are Shown.

| Treatment | Sample No. | pat | yfp |
|---|---|---|---|
| QD-R9-Plasmid DNA Complex | 1 | + | + |
|  | 2 | + | − |
|  | 3 | + | − |
| QD-γZEIN-Plasmid DNA Complex | 4 | + | − |
|  | 5 | + | − |
|  | 6 | + | − |
|  | 7 | + | − |
|  | 8 | + | − |
|  | 9 | + | + |
|  | 10 | + | + |
| QD-MPB-Plasmid DNA Complex | 11 | + | − |
|  | 12 | + | + |
|  | 13 | + | + |
|  | 14 | + | + |
|  | 15 | + | + |
| Control Rxns |  | − | − |

Example 2

Live Imaging in Planta Via Quantum Dot Cell Penetrating Peptide Conjugates

Live Imaging via DHLA-Capped QD and QD-CPP Conjugate

Fusion proteins consisting of Cell Penetrating Peptides (CPP) and Yellow Fluorescent Protein (YFP) were produced and isolated as previously described in U.S. Provisional Patent No. 61/319,764 and Chen et al., 2007. The various cell penetrating peptides were sub-cloned up-stream of the YFP coding sequence at unique NcoI-SpeI restriction sites within a pET280 bacterial expression vector. Expression of the proteins was induced, and they were isolated and purified as described in U.S. Provisional Patent No. 61/319,764 and Chen et al., 2007. The sequences of the CPP-YFP fusions are listed in Table 3.

TABLE 3

Nucleotide Sequences of Cell Penetrating Peptide and Yellow Fluorescent Protein Fusions

| Name | SEQ ID NO: | Sequence |
|---|---|---|
| TAT-YFP | SEQ ID NO: 8 | atgtatggccgcaaaaaacgccgccagcgccgccgccatcatcatcatcatcatg gatccagcggcgccctgctgttccacggcaagatcccctacgtggtggagatgga gggcaatgtggatggccacaccttcagcatccgcggcaagggctacggcgatgc cagcgtgggcaaggtggatgcccagttcatctgcaccaccggcgatgtgcccgtg ccctggagcacccctggtgaccaccctgacctacggcgcccagtgcttcgccaagt acggccccgagctgaaggatttctacaagagctgcatgcccgatggctacgtgca ggagcgcaccatcaccttcgagggcgatggcaatttcaagacccgcgccgaggt gaccttcgagaatggcagcgtgtacaatcgcgtgaagctgaatggccagggcttc aagaaggatggccacgtgctgggcaagaatctggagttcaatttcacccccact gcctgtacatctggggcgatcaggccaatcacggcctgaagagcgccttcaagat ctgccacgagatcaccggcagcaagggcgatttcatcgtggccgatcacaccca gatgaatacccccatcggcggcggcccgtgcacgtgcccgagtaccaccacat gagctaccacgtgaagctgagcaaggatgtgaccgatcaccgcgataatatgagc ctgaaggagaccgtgcgcgccgtggattgccgcaagacctacctgtga |
| MPG-YFP | SEQ ID NO: 9 | atgggcgcgctgtttctgggcttctgggcgcggcgggcagcaccatgggcgcgt ggagccagccgaaaaaaaaacgcaaagtgcatcatcatcatcatcatggatccag cggcgccctgctgttccacggcaagatcccctacgtggtggagatggagggcaat gtggatggccacaccttcagcatccgcggcaagggctacggcgatgccagcgtg ggcaaggtggatgcccagttcatctgcaccaccggcgatgtgcccgtgccctgga gcacccctggtgaccaccctgacctacggcgcccagtgcttcgccaagtacggcc ccgagctgaaggatttctacaagagctgcatgcccgatggctacgtgcaggagcg caccatcaccttcgagggcgatggcaatttcaagacccgcgccgaggtgaccttc gagaatggcagcgtgtacaatcgcgtgaagctgaatggccagggcttcaagaag gatggccacgtgctgggcaagaatctggagttcaatttcacccccactgcctgta catctggggcgatcaggccaatcacggcctgaagagcgccttcaagatctgccac gagatcaccggcagcaagggcgatttcatcgtggccgatcacacccagatgaata cccccatcggcggcggcccgtgcacgtgcccgagtaccaccacatgagctacc acgtgaagctgagcaaggatgtgaccgatcaccgcgataatatgagcctgaagg agaccgtgcgcgccgtggattgccgcaagacctacctgtga |

TABLE 3 -continued

Nucleotide Sequences of Cell Penetrating Peptide and Yellow Fluorescent Protein Fusions

| Name | SEQ ID NO: | Sequence |
| --- | --- | --- |
| γ-ZEIN-YFP | SEQ ID NO: 10 | atggtgcgtctgcctcctccagttcgtctgccacctcctgtacgtctgccgccaccg caccatcaccaccaccacggctcctctggtgcgctgctgttccacggcaaaatccc gtacgtggtggagatggaaggcaacgttgatggtcatacttttagcatccgtggca aaggctatggcgatgcctctgtcggcaaggttgatgcgcagttcatctgcaccact ggtgatgttccggttccatggtctaccctggttactaccctgacgtacggtgcgcag tgtttcgctaaatacggcccggagctgaaagacttctacaaatcttgtatgccggat ggttatgtacaggaacgtaccatcacttcgagggtgatggtaacttcaaaacccgt gcggaggttaccttcgaaaacggcagcgtgtataaccgtgttaaactgaacggcc agggtttcaagaaagacggccatgtcctgggtaaaaacctggaattcaacttcacc ccgcactgtctgtacatttggggcgaccaagctaaccatggcctgaaatccgctttc aaaatctgccacgaaatcactggttccaaaggtgacttcattgtagcagatcacacc cagatgaatactccaatcggtggcggtccagttcatgtaccggagtatcatcatatg agctatcacgtgaaactgagcaaggatgttaccgatcaccgcgataatatgagcct gaaagagactgtgcgtgcggtggactgccgtaaaacgtatctgtaa |
| PEP1-YFP | SEQ ID NO: 11 | atgaaagaaacgtggtgggaaacttggtggactgaatggagccaaccgaagaaa aagcgtaaagtacaccatcatcaccaccatggttcctctggtgctctgctgttccac ggtaaaatcccgtatgtggtggaaatggaaggtaacgtagacggtcacaccttctc tattcgcggcaagggttacggtgacgcatctgtaggtaaggtcgacgcccagtttat ctgtaccactggtgacgttccggttccatggtctactctggttactaccctgacgtatg gcgcccagtgctttgcgaaatacggcccggagctgaaggacttttacaaatcttgta tgccggacggttacgtccaggagcgcaccattactttcgaaggtgatggtaacttta aaacgcgtgccgaggtcacttttgagaacggctctgtgtataaccgcgtgaagctg aacggccagggttttaaaaaagatggtcacgttctgggtaagaatctggagttcaa ctttacgccgcattgcctgtacatttggggtgatcaggctaaccatggtctgaaatct gcttttaagatttgccacgagatcaccggttctaaaggcgattttattgtagcagatca cacccagatgaacactccaatcggtggtggcccagtgcacgtgccggagtatcac catatgagctatcacgttaagctgtccaaagacgtcacggatcaccgtgataatatg tccctgaaagagaccgtccgcgccgtggactgccgtaaaacctatctgtaa |
| R9-YFP | SEQ ID NO: 12 | atgcgtcgtcgccgccgtcgccgtcgtcgtcatcatcaccaccatcacggctcttcc ggtgccctgctgttccacggtaaaattccgtatgtggttgagatggagggtaatgtt gatggccatactttctccatccgcggcaaaggttatggcgacgcgtctgttggtaaa gtggacgcacaattcatttgtaccaccggcgatgtgccggtgccgtggagcaccct ggtgaccacgctgacttacggtgcgcagtgctttgctaaatacggtccggagctga aagacttctacaaatcctgcatgccggacggctacgtgcaagagcgtaccatcac ctttgagggcgacggcaacttcaaaacccgcgcagaggttaccttcgagaatggtt ctgtgtataaccgcgtcaaactgaacggccagggcttcaaaaaggacggccacgt cctgggcaaaaacctggagttcaacttcaccccgcattgtctgtacatttgggcga tcaggctaatcacggtctgaaatctgcgttcaaaatctgtcacgagatcacgggttct aaaggtgatttcatcgtcgcggaccatactcagatgaacacgccgattggcggtgg tccggtgcatgttccggagtaccaccacatgtcttaccacgtgaaactgtctaaaga cgtaactgaccaccgtgacaacatgtctctgaaagaaaccgtccgtgctgtagact gccgtaagacctatctgtga |

DHLA-capped QDs with an emission maxima centered at 620 nm were synthesized using stepwise reactions of organometallic precursors in hot coordinating solvent mixtures following procedures previously described. See Aron et al., 2006; Lu et al., 2007; Doyon et al., 2006; Collins et al., 2003; and Lanio et al., 2000. The nanocrystals were made hydrophilic by exchanging the native capping shell, composed primarily of trioctyl phosphine (TOP) and trioctyl phosphine oxide (TOPO) with bifunctional ligands as previously described. see Lie et al., 2002; Mani et al., 2006; Desjarlais and Berg, 1993. Two sets of hydrophilic QDs were used (1) nanocrystals capped with dihydrolipoic acid, and (2) nanocrystals capped with a mixture of polyethylene glycol (Mw~600) appended dihydrolipoic acid (DHLA-PEG) and biotin terminated DHLA polyethylene glycol (Mw~400) (DHLA-PEG-biotin) with a 9:1 molar ratio of the ligands. The resulting QDs were referred to as DHLA-QDs and DHLA-PEG-biotin-QDs, respectively.

In addition to the CPP molecules described above (γ-ZEIN, MPG, and R9), two additional molecules, PEP1 and TAT (Table 4), were assembled with the DHLA-capped QDs using the protocol described previously (Aron et al., 2006). QD-CPP conjugates of appropriate molar ratios as described above were added to 0.3 µM of 510-620 nm emitting DHLA-capped QDs in 10 mM Tris-Cl pH 8.0 buffer and incubated at room temperature for 30 minutes. The conjugates were characterized using gel electrophoresis, where a change in the electrophoretic mobility of QDs assembled with CPPs was observed. Samples were diluted in 1×TBE buffer (0.09 M Tris, 0.002 M Nae-EDTA, 0.09 M Boric acid, pH 8.3) and run on 1% or 2% agarose gels. The effect of varying the number of CPP molecules per QD was monitored by observing the fluorescence of the complex. Gel images were produced by exciting the QD and/or protein and observing the images for separated fluorescent bands within the gels. In addition, conjugate formation was confirmed by monitoring changes in the energy transfer between the QDs and CPPs upon self-assembly.

TABLE 4

Amino Acid Sequences and Molecular Masses of the Synthesized Peptides

| SEQ ID NO: | Peptide | Sequence | Molecular Wt |
|---|---|---|---|
| SEQ ID NO: 1 | R9 | RRRRRRRRR | 14.23 |
| SEQ ID NO: 2 | MPG | GALFLGFLGAAGSTMGAWSQPKKKRKV | 28.07 |
| SEQ ID NO: 3 | γ-ZEIN | VRLPPP VRLPPP VRLPPP | 19.98 |
| SEQ ID NO: 13 | PEP1 | MKETWWETWWTEWSQPKKKRKV | 2848.3 |
| SEQ ID NO: 14 | TAT | YGRKKRRQRRR | 1559.9 |

Uptake and Sub-Cellular Localization of Quantum Dot-CPP Conjugate within Plant Cells QD bioconjugates were diluted with complete culture medium and added to *Arabidopsis* cluster cell cultures, JTNT1 tobacco and carrot (U.S. Provisional Patent No. 61/319,764) single cell cultures with intact walls. The solution was incubated at 37° C. for 1-4 hours at 40-150 µg/ml. Mixed QD conjugates consisting of either 1:5 or 1:10 QD/CPP ratios at 50 CPP molecules per QD, were incubated with the cell cultures. Excess unbound QD conjugates were removed by washing the culture at least three times with 1×PBS or cell culture medium. Cells were then incubated for 30 minutes at room temperature and washed twice with PBS.

Epifluorescence image collection was carried out using a Leica confocal microscope. Side-by-side split fluorescence images were collected and quantitated using a dual view system equipped with a 565 nm dichroic filter. For 620 nm QDs, the QD-CPP complex was imaged. Cellular imaging, samples were excited at 488 nm and emissions were collected/separated with the 565 nm dichroic filter and deconvoluted. QD fluorescence was collected at λ<620 nm and the YFP fluorescent tail collected at λ>537 nm if CPP fusion tag is alone used without the QDs. YFP leakage into the QD window is subtracted as part of the deconvolution. The 620 nm QDs alone are excited at 488 nm and their respective emissions are separated with the 565 nm dichroic filter and deconvoluted. DAPI and Calcuofluor fluorescence is excited using a xenon (Xe) lamp and emission collected using a DAPI cube (D350/50X for excitation, dichroic 400DCLP, D460/50m for detection). AF647-TF is excited using the Xe lamp and fluorescence detected using a Cy5 cube (excitation HQ620/60X, dichroic Q660LP, emission HQ700/75m). Both excitation/detection cubes are provided by Chroma Technology (Bellows Falls, Vt.). Differential interference contrast (DIC) images are collected using a bright light source.

Thus the functionalized QD containing different cell penetrating peptides to track localization in single walled cells of *Arabidopsis*, carrot and JTNT1 tobacco cells were observed with LSM710 Zeiss confocal microscope imaging. QDs have higher resistance to metabolic degradation and higher resistance to photobleaching QD amines complexed with CPPs such as R9, MPG, γ-ZEIN, PEP1 and TAT were incubated with single cells of *Arabidopsis*, carrot and JTNT1 for 30 minutes and cells were washed with medium and imaged using a LSM710 Zeiss confocal microscope. A Zeiss LSM710 confocal scanner equipped with Axio Observer Z1 inverted microscope was used with excitation wavelength for a 3-hour uptake experiment, and the excitation wavelength of 561 nm was used for a 5-hour uptake experiment.

The results indicated that the live *Arabidopsis*, JTNT1 tobacco and carrot suspension cells with intact walls did not show the fluorescence at λ=620 nm. However, when $QD^{620}$ were introduced into the cells, the internalization of the QD into the plant cells was observed. Images of channels taken in the Blue and Red emission for Calcofluor, the cell wall stain and $QD^{620}$ fluorescent range respectively showed blue fluorescence indicating the presence of cell wall or red fluorescence indicating the presence of the nucleus where the $QD^{620}$ is localized due to targeting in the nucleus. An overlay of all the images illustrated that the internalized QDs were concentrated in the cytoplasm and the nucleus.

Targeting of CPP conjugated $QD^{620}$ into the nucleus of *Arabidopsis*, JTNT1, and carrot suspension cells was demonstrated. The targeting of the nucleus was confirmed by counterstaining the nucleus with the nuclear stain, DAPI. DAPI is a vital nuclear stain, quite commonly used in living plant cells. This stain is a fluorescent stain that is excited by ultraviolet light, showing blue fluorescence when bound to DNA in the nucleus. Though the Calcofluor emission range is in blue, it is only specific to the wall. Overlay of images of the $QD^{620}$ CPP conjugates and DAPI stained images showed the co-localization of the QD-MPG conjugates in the nucleus.

The internalized $QD^{620}$ conjugated with MPG, R9, γ-ZEIN, PEP1 and TAT CPPs have characterized surface charges values and their zeta potential values were measured in the range of 9.5466-10.1586 my. The hydrodynamic values of the conjugate sizes were in the range of 122-342 nm. When these particle conjugates were incubated with the *Arabidopsis*, JTNT1 tobacco and carrot suspension cells the conjugates were internalized into the intact cells, and are localized in the nucleus indicating the nuclear targeting of QD conjugates in the live cells as opposed to just the treatment with $QD^{620}$ amine conjugate alone where the particles are seen in mostly cytoplasm and occasionally in the nucleus. The translocation into the nucleus of *Arabidopsis*, JTNT1 tobacco and carrot cells were observed with Quantum Dots complexed to the Cell Penetrating Peptides (MPG, TAT, PEP1, R9, and γ-zein).

This example exemplifies the use of QDs tagged with Cell Penetrating Peptides as fluorescent particle carriers for live cell tracking studies. The QDs function as stable beacons.

Example 3

Live Imaging in Planta Via Polystyrene Cell Penetrating Peptide Conjugates

The delivery and cellular localization of polystyrene nanoparticles fused with CPPs was completed. The complexed polystyrene/CPP nanoparticles were translocated into live plant cells and targeted to specific cell compartments.

Internalization of polystyrene nanoparticles was labeled with the Cell Penetrating Peptide, TAT, in JTNT1 tobacco single cells.

Conjugation of Tat Peptide to Carboxylated FluoSpheres

Evaluation of the uptake of FluoSphere fluorescent polystyrene nanoparticles (20 nm diameter) into walled JTNT1 tobacco single cells was tested with and without a partial TAT cell penetrating peptide.

FluoSpheres (Invitrogen, Carlsbad, Calif.) were obtained from 4° C. storage and prepared by adding 1-Ethyl-3-[3-dimethylaminopropyl]carbodiimide hydrochloride (EDCL) and N-hydroxysuccinimide (NHS). The resulting cocktail was incubated for 1 hour to allow the EDCL to react with the FluoSpheres. The TAT cell penetrating peptide (with a ter-tert butanol protected carboxy terminus) was complexed with the FluoSpheres. The TAT-FluoSphere complex was incubated overnight at room temperature to form a complex. The complex was purified using an Amicon, Ultra-4 Centrifugal Filter Units with 50,000 molecular weight cut-off limit. The retained TAT-FluoSphere complex was transferred to a clean vial. The TAT-FluoSphere complex was stored at 4° C. until needed for experiments.

Cell Uptake Studies with TAT-Fluospheres and Unconjugated Fluospheres in JTNT1 Tobacco Suspension Cells JTNT1 single cell suspensions were prepared in NT1B medium, adjusted to contain 3% glycerol. 200 of freshly sonicated and vortexed Tat-FluoSpheres and uncomplexed FluoSpheres were added to the JTNT1 cells and incubated for 30, 60, or 120 minutes. The JTNT1 single cells were isolated by centrifuging the tubes for 5 minutes at 700 rpm. The supernatant was removed and cells rinsed two times using 2 mL portions of NT1B. The washed JTNT1 cells were resuspended in 1 mL of the glycerol-containing NT1B medium and some of the cells were pipetted onto separate glass slides and visualized using an upright fluorescence microscope in brightfield mode and containing a filter cube set for recording fluorescence emission at 580 nm. The microscope was used to capture images of the JTNT1 cells which had been treated with the TAT-FluoSphere complex. ImageJ software was used to display and overlay (stack) the brightfield and fluorescence images for ease of determination of the location of FluoSpheres within the JTNT1 tobacco cells.

The TAT-FluoSphere complex 120 minute treatment of the JTNT1 tobacco cells resulted in internalization of the TAT-FluoSphere complex and targeting into the nucleus of cells. The 30 minute treatment did not result in significant cell uptake of the TAT-FluoSphere complex. It was noted that some TAT-FluoSphere complex was associated with the JTNT1 glycerol single cell walls. The 60 minutes treatment of the TAT-FluoSpheres complex resulted in the internalization of some of the complex within the JTNT1 single cells. A large number of the observed TAT-FluoSphere complex were observed at the near the periphery of the cells, however a few of the complexes appeared in close proximity to the nucleus of the JTNT1 tobacco cells. After 120 minutes of treatment, a significant number of the TAT-FluoSpheres complex were uptaken within the JTNT1 tobacco cells, and targeted to the nucleus of these cells.

Internalization of Polystyrene nanoparticles was labeled with TAT, MPG, and γ-ZEIN Cell Penetrating Peptides (CPPS) in *Arabidopsis* suspension cells.

Conjugation of Cell Penetrating Peptides to Carboxylated Fluospheres and Cellular Uptake into *Arabidopsis* Suspension Cells Different types of CPPs were labeled to evaluate nanoparticle uptake across cell walls and cell membranes into the cytoplasm and nuclei of live *Arabidopsis* suspension cells using confocal microscopy. FluoSpheres were complexed with cell penetrating peptides (TAT, MPG, and λ-zein) as described above. The resulting CPP-FluoSphere complex was mixed with 0.1 mL of *Arabidopsis* aggregate cell suspension and incubated at room temperature in the dark for 3 hours (first experiment) or for 5 hours (second experiment). The cell suspensions were centrifuged and the supernatant was removed. The cells were resuspended in fresh culture medium. A drop of the resuspended cell suspensions were pipetted onto a glass coverslip, and vacuum grease was used to form a perimeter around the cell suspension droplet before placing a second glass coverslip atop the cell suspension to form a sandwich of cells between the two coverslips. A confocal microscope (Zeiss LSM710 confocal scanner equipped with Axio Observer Z1 inverted microscope with excitation wavelength of 514 nm for 3-hour uptake experiment, and 561 nm for 5-hour uptake experiment) was used to image the *Arabidopsis* aggregate cells 3 hours and 5 hours post-exposure to the CPP-FluoSphere complex.

*Arabidopsis* aggregate cells exhibited no apparent autofluorescence when excited at 561 nm and 514 nm by the laser on the confocal microscope. However, *Arabidopsis* protoplasts exhibited some autofluorescence at this wavelength. The background autofluorescence of the cells did not interfere with the imaging of the CPP-FluoSphere complex uptake experiments.

*Arabidopsis* protoplasts 5 hours post-exposure with CPP-FluoSpheres conjugates were imaged and then counterstained with a Calcofluor dye. CPP-FluoSpheres conjugates were internalized by the protoplasts, even though the protoplasts were regenerating cell wall materials. Cells were determined to be alive as evidenced by active protoplast strands when observed under confocal microscopy. In addition, a single cell was observed to uptake the TAT cell penetrating peptide FluoSphere complex in the nucleus of the cell. *Arabidopsis* aggregate cells after 5-hour post-exposure with the γ-zein cell penetrating peptide FluoSphere conjugates indicated were observed to contain FluoSpheres within the cell nuclei. These images indicated that the γ-zein cell penetrating peptide mediated transport of the FluoSpheres into the cell nuclei.

*Arabidopsis* protoplasts observed 6 hours post-exposure to unmodified FluoSpheres and counter-stained with Calcofluor did not internalize into the *Arabidopsis* protoplasts and were not transported to cell nuclei. Observations noted the collapsed and dead protoplast association with unmodified FluoSpheres. Thus it was demonstrated that the unmodified FluoSpheres were not translocated into the cell of the live *Arabidopsis* protoplasts. However, the collapsed cells or dead cells internalized the unmodified FluoSpheres. This observation indicates that when the membrane integrity of the cells is compromised unmodified FluoSpheres are internalized, but unmodified FluoSpheres are not internalized into living cells that possess an intact cell wall and cell membrane.

These examples show that CPP fusion tags provide for efficient delivery and targeting into the cell. Moreover, depending on the type of CPP used, the nuclei can be specifically targeted. The use of these CPP-Fluosphere conjugants can facilitate the uptake of cell-impermeable macromolecules. Although the use of this approach allows cellular labeling using fewer QDs or polystyrene NPs, it is still dependent on the endocytic ability of cells, as labeling was abrogated in cells incubated at 4° C. or incubated with an inhibitor such as Wortmannin PAMAM-TRITC Labeled Dendrimer Conjugates Used as Novel Probes for In Vivo Imaging of Sub-Cellular Compartments in *Arabidopsis* Plant Cells.

A nanoparticle based beacon that can be used to quantify endocytosis in intact, walled living cells can permit the imaging of the organelles involved in plant endocytosis in vivo.

Moreover, this imaging is accomplished without fading or bleaching of the dye. Finally tracking of the particle or cargo delivery in the live plant cells can be accomplished with such a nanoparticle based beacon.

This example presents the imaging of an endocytic compartment in live plant cells with a PAMAM Dendrimer-TRITC labeled particles. The use of these particles for live imaging instead of styryl dyes such as FM4-64, that are known to be used in plant vacuolar trafficking and endocytosis studies. They are known to move from one compartment to another over the course of time, thus providing an effective means of imaging endocytotic compartments within live plant cells. However, it is possible to use a fluorescently labeled PAMAM dendrimer particle to show the endocytotic behavior, and biomolecules can be tagged or tethered as cargos on Dendrimers to study trafficking in live plant cells (unlike the styryl dyes which only stains the vesicles). The wortmannin treatment inhibited the endocytosis in this study demonstrating that the PAMAM dendrimer particle coats the endosome vesicles and could be used as a beacon in vesicular tracking studies. The PAMAM Dendrimer-TRITC labeled particles use for tracking endocytosis was demonstrated, and inhibition of endocytosis resulted with the use of wortmannin. Thus providing an example of a novel role for the particle as beacons in live cell imaging for vesicular tracking studies in plant cells.

TRITC Labeling and PAMAM Dendrimer

The TRITC labeled PAMAM dendrimer were labeled according to Pasupathy et al., 2008. The TRITC labeled PAMAM dendrimer was added to a 0.5 ml aliquot of *Arabidopsis thaliana* suspension cells from 7 day old cultures. In addition, the Calcofluor stain was added to the mixture, 5 minutes prior to imaging. The plant cultures were incubated for 30 minutes with the TRITC-Dendrimer complexes and then they were immediately examined under the confocal microscope. For several control samples, 25 µL of 10 µM wortmannin (MP Biomedicals, Solon, Ohio) was added to the culture, 30 minutes prior to adding TRITC-Dendrimer complexes. The samples were then incubated again for 30 minutes. The live cells and clusters were imaged using LSM710 Confocal microscope, following the protocol described above. Control cells which were not incubated with dendrimers did not produce a background when viewed via confocal microscopy.

Confocal Laser Scanning Microscopy (CLSM)

To observe the cellular association of TRITC-PAMAM complexes in the treated cells treated and to view the untreated control with the respective incubation time duration, the cells were rinsed with culture medium or PBS buffer (pH 7.4) twice and Calcofluor was added to stain the cell wall for 5 minutes and then immediately examined under the confocal microscope. Cells were observed by CLSM (Carl Zeiss LSM-710, Germany) with an argon laser of 600-620 nm to image the cells live. Here, the intracellular distribution of TRITC-PAMAM was observed in a single plane and also as z-sections.

The results from the Wortmanin untreated cells showed that the membranes of cells and endosomes were stained with the TRITC labeled PAMAM Dendrimer. The TRITC labeled PAMAM dendrimers were transported into the endosomes. It was possible to track the PAMAM Dendrimer within the endosomes of the cells translocated across the intact cell wall via the confocal laser scanning microscope. The PAMAM Dendrimer was translocated into the cell through the process of endocytosis. In the presence of Wortmannin the TRITC labeled PAMAM Dendrimer localized in the membrane of the cell. Because the endocytosis process was inhibited, the PAMAM Dendrimer-CPP complex did not translocate into the cytosol of the *Arabidopsis* cells.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims and their equivalents.

What may be claimed is:

1. A method of introducing a nucleic acid of interest into a plant cell having a cell wall to effect stable transformation of a plant cell, the method comprising:
   providing the plant cell having a cell wall;
   interacting a quantum dot (QD) with a cell penetrating peptide (CPP) to form a QD-peptide conjugate;
   attaching one or more nucleic acids of interest to the CPP to form an activated QD-peptide conjugate;
   placing the cell having a cell wall and the activated QD-peptide conjugate in contact with each other;
   allowing uptake of the QD-peptide conjugate and the one or more nucleic acids of interest into the cell having the cell wall; and
   selecting cells that have stably integrated the one or more nucleic acids of interest.

2. The method according to claim 1, wherein interacting a QD with the CPP comprises assembly of the CPP onto the surface of the QD.

3. The method according to claim 1, wherein attaching one or more nucleic acids of interest to the CPP comprises interacting negatively charged groups of the one or more nucleic acids with amino groups at a C-terminal end of the CPP.

4. The method according to claim 1, further comprising allowing uptake of the QD-peptide conjugate into a compartment of the plant cell comprising a cell wall.

5. The method according to claim 4, wherein the compartment is selected from the group consisting of cytosol, nucleus, tonoplasts, plastid, etioplast, chromoplast, leucoplast, elaioplast, proteinoplast, amyloplast, chloroplast, and the lumen of the double membrane.

6. The method according to claim 1, wherein the plant cell comprising a cell wall is selected from the group consisting of tobacco, carrot, maize, canola, rapeseed, cotton, palm, peanut, soybean, *Oryza* sp., *Arabidopsis* sp., *Ricinus* sp., and sugarcane cells.

7. The method according to claim 1, wherein the plant cell is from a tissue selected from the group consisting of embryo, meristematic, callus, pollen, leaves, anthers, roots, root tips, flowers, seeds, pods and stems.

8. The method according to claim 1, wherein the CPP is selected from the group consisting of R9, MPG, TAT and γ-Zein peptides.

9. The method of claim 1, where the one or more nucleic acids of interest is selected from the group consisting of DNA, RNA, RNAi molecules, genes, plasmids, cosmids, YACs, BACs, and combinations thereof.

10. The method according to claim 9, wherein the nucleic acid of interest comprises a gene.

11. The method according to claim 10, wherein the gene is a foreign protein gene, an agronomic gene, or a marker gene.

12. The method according to claim 9, where the selected cells are regenerable cells.

13. The method according to claim 12, further comprising regenerating a plant from the regenerable cells.

14. A method of stably expressing a gene, the method comprising:
   providing a plant cell having a cell wall;
   interacting a quantum dot (QD) with a cell penetrating peptide (CPP) to form a QD-peptide conjugate;
   attaching one or more genes to the CPP to form an activated QD-peptide conjugate;
   placing the cell having a cell wall and the activated QD-peptide conjugate in contact with each other;
   allowing uptake of the QD-peptide conjugate and the one or more genes into the cell having the cell wall; and selecting for cells stably expressing the gene to produce a progeny plant;

thus expressing the gene in progeny of a plant having the plant cell.

15. The method according to claim 14, wherein the gene is expressed in a chloroplast.

16. A method for transferring a gene into a plant cell, comprising:

interacting a quantum dot (QD) with a cell penetrating peptide (CPP) to form a QD-peptide conjugate;

interacting the QD-peptide conjugate with a plasmid DNA comprising one or more genes to form an activated QD-peptide conjugate structure; and contacting the activated QD-peptide conjugate structure with an intact wall-bearing plant cell under conditions permitting the uptake of the CPP and the one or more genes from the plasmid DNA into the plant cell.

17. The method of claim 16, further comprising selecting for cells stably expressing the gene to produce a progeny plant;

thus stably expressing the gene in progeny of a plant having the plant cell.

18. A method of screening and identifying plant transformants, comprising;

providing a plant cell having a cell wall;

interacting a quantum dot (QD) with a cell penetrating peptide (CPP) to form a QD-peptide conjugate;

attaching one or more nucleic acids of interest to the CPP to form an activated QD-peptide conjugate;

placing the cell having a cell wall and the activated QD-peptide conjugate in contact with each other;

allowing uptake of the QD-peptide conjugate and the one or more nucleic acids of interest into the cell having the cell wall; and imaging the plant cell having the cell wall.

* * * * *

SEQUENCE LISTING

```
<160> NUMBER OF SEQ ID NOS: 14

<210> SEQ ID NO 1
<211> LENGTH: 9
<212> TYPE: PRT
<213> ORGANISM: Artificial
<220> FEATURE:
<223> OTHER INFORMATION: R9 Cell Penetrating Peptide

<400> SEQUENCE: 1

Arg Arg Arg Arg Arg Arg Arg Arg Arg
1               5

<210> SEQ ID NO 2
<211> LENGTH: 27
<212> TYPE: PRT
<213> ORGANISM: Artificial
<220> FEATURE:
<223> OTHER INFORMATION: MPG Peptide

<400> SEQUENCE: 2

Gly Ala Leu Phe Leu Gly Phe Leu Gly Ala Ala Gly Ser Thr Met Gly
1               5                   10                  15
```

Ala Trp Ser Gln Pro Lys Lys Lys Arg Lys Val
            20                  25

<210> SEQ ID NO 3
<211> LENGTH: 6
<212> TYPE: PRT
<213> ORGANISM: Artificial
<220> FEATURE:
<223> OTHER INFORMATION: gamma-Zein Peptide

<400> SEQUENCE: 3

Val Arg Leu Pro Pro Pro
1               5

<210> SEQ ID NO 4
<211> LENGTH: 24
<212> TYPE: DNA
<213> ORGANISM: Artificial
<220> FEATURE:
<223> OTHER INFORMATION: YFP Primer

<400> SEQUENCE: 4
tgttccacgg caagatcccc tacg                                           24

<210> SEQ ID NO 5
<211> LENGTH: 24
<212> TYPE: DNA
<213> ORGANISM: Artificial
<220> FEATURE:
<223> OTHER INFORMATION: YFP Primer

<400> SEQUENCE: 5
tattcatctg ggtgtgatcg gcca                                           24

<210> SEQ ID NO 6
<211> LENGTH: 24
<212> TYPE: DNA
<213> ORGANISM: Artificial
<220> FEATURE:
<223> OTHER INFORMATION: PAT Primer

<400> SEQUENCE: 6
ggagaggaga ccagttgaga ttag                                           24

<210> SEQ ID NO 7
<211> LENGTH: 24
<212> TYPE: DNA
<213> ORGANISM: Artificial
<220> FEATURE:
<223> OTHER INFORMATION: PAT Primer

<400> SEQUENCE: 7
agatctgggt aactggccta actg                                           24

<210> SEQ ID NO 8
<211> LENGTH: 759
<212> TYPE: DNA
<213> ORGANISM: Artificial
<220> FEATURE:
<223> OTHER INFORMATION: TAT Peptide-YFP Fusion Protein

<400> SEQUENCE: 8
atgtatggcc gcaaaaaacg ccgccagcgc cgccgccatc atcatcatca tcatggatcc     60
agcggcgccc tgctgttcca cggcaagatc ccctacgtgg tggagatgga gggcaatgtg    120
gatggccaca ccttcagcat ccgcggcaag ggctacggcg atgccagcgt gggcaaggtg    180

```
gatgcccagt tcatctgcac caccggcgat gtgcccgtgc cctggagcac cctggtgacc    240
accctgacct acggcgccca gtgcttcgcc aagtacggcc ccgagctgaa ggatttctac    300
aagagctgca tgcccgatgg ctacgtgcag gagcgcacca tcaccttcga gggcgatggc    360
aatttcaaga cccgcgccga ggtgaccttc gagaatggca cgtgtacaa tcgcgtgaag    420 ctgaatggcc agggcttcaa gaaggatggc cacgtgctgg gcaagaatct ggagttcaat    480
ttcacccccc actgcctgta catctgggc gatcaggcca tcacggcct gaagagcgcc    540 ttcaagatct gccacgagat caccggcagc aagggcgatt tcatcgtggc cgatcacacc    600
cagatgaata cccccatcgg cggcggcccc gtgcacgtgc cgagtacca ccacatgagc    660 taccacgtga agctgagcaa ggatgtgacc gatcaccgcg ataatatgag cctgaaggag    720
accgtgcgcg ccgtggattg ccgcaagacc tacctgtga                          759

<210> SEQ ID NO 9
<211> LENGTH: 807
<212> TYPE: DNA
<213> ORGANISM: Artificial
<220> FEATURE:
<223> OTHER INFORMATION: MPG Peptide-YFP Fusion Protein

<400> SEQUENCE: 9
atgggcgcgc tgtttctggg ctttctgggc gcggcgggca gcaccatggg cgcgtggagc     60
cagccgaaaa aaaaacgcaa agtgcatcat catcatcatc atggatccag cggcgccctg    120
ctgttccacg gcaagatccc ctacgtggtg gagatggagg gcaatgtgga tggccacacc    180
ttcagcatcc gcggcaaggg ctacggcgat gccagcgtgg gcaaggtgga tgcccagttc    240
atctgcacca ccggcgatgt gcccgtgccc tggagcaccc tggtgaccac cctgacctac    300
ggcgcccagt gcttcgccaa gtacggcccc gagctgaagg atttctacaa gagctgcatg    360
cccgatggct acgtgcagga gcgcaccatc accttcgagg gcgatggcaa tttcaagacc    420
cgcgccgagg tgaccttcga gaatggcagc gtgtacaatc gcgtgaagct gaatggccag    480
ggcttcaaga aggatggcca cgtgctgggc aagaatctgg agttcaattt cacccccac    540 tgcctgtaca tctggggcga tcaggccaat cacggcctga gagcgcctt caagatctgc    600 cacgagatca ccggcagcaa gggcgatttc atcgtggccg atcacaccca gatgaatacc    660
cccatcggcg cggcccccgt gcacgtgccc gagtaccacc acatgagcta ccacgtgaag    720
ctgagcaagg atgtgaccga tcaccgcgat aatatgagcc tgaaggagac cgtgcgcgcc    780
gtggattgcc gcaagaccta cctgtga                                       807

<210> SEQ ID NO 10
<211> LENGTH: 780
<212> TYPE: DNA
<213> ORGANISM: Artificial
<220> FEATURE:
<223> OTHER INFORMATION: gamma-Zein-YFP Fusion Protein

<400> SEQUENCE: 10
atggtgcgtc tgcctcctcc agttcgtctg ccacctcctg tacgtctgcc gccaccgcac     60
catcaccacc accacggctc ctctggtgcg ctgctgttcc acggcaaaat cccgtacgtg    120
gtggagatgg aaggcaacgt tgatggtcat acttttagca tccgtggcaa aggctatggc    180
gatgcctctg tcggcaaggt tgatgcgcag ttcatctgca ccactggtga tgttccggtt    240
ccatggtcta ccctggttac taccctgacg tacggtgcgc agtgtttcgc taaatacggc    300
ccggagctga aagacttcta caaatcttgt atgccggatg gttatgtaca ggaacgtacc    360
```

```
atcactttcg agggtgatgg taacttcaaa acccgtgcgg aggttacctt cgaaaacggc    420
agcgtgtata accgtgttaa actgaacggc cagggtttca agaaagacgg ccatgtcctg    480
ggtaaaaacc tggaattcaa cttcaccccg cactgtctgt acatttgggg cgaccaagct    540
aaccatggcc tgaaatccgc tttcaaaatc tgccacgaaa tcactggttc caaaggtgac    600
ttcattgtag cagatcacac ccagatgaat actccaatcg gtggcggtcc agttcatgta    660
ccggagtatc atcatatgag ctatcacgtg aaactgagca aggatgttac cgatcaccgc    720
gataatatga gcctgaaaga gactgtgcgt gcggtggact gccgtaaaac gtatctgtaa    780
```

<210> SEQ ID NO 11
<211> LENGTH: 789
<212> TYPE: DNA
<213> ORGANISM: Artificial
<220> FEATURE:
<223> OTHER INFORMATION: PEP1 Peptide-YFP Fusion Protein

<400> SEQUENCE: 11

```
atgaaagaaa cgtggtggga acttggtgg actgaatgga gccaaccgaa gaaaaagcgt    60
aaagtacacc atcatcacca ccatggttcc tctggtgctc tgctgttcca cggtaaaatc    120
ccgtatgtgg tggaaatgga aggtaacgta gacggtcaca ccttctctat tcgcggcaag    180
ggttacggtg acgcatctgt aggtaaggtc gacgcccagt ttatctgtac cactggtgac    240
gttccggttc catggtctac tctggttact accctgacgt atggcgccca gtgctttgcg    300
aaatacggcc cggagctgaa ggacttttac aaatcttgta tgccggacgg ttacgtccag    360
gagcgcacca ttactttcga aggtgatggt aactttaaaa cgcgtgccga ggtcactttt    420
gagaacggct ctgtgtataa ccgcgtgaag ctgaacggcc agggttttaa aaagatggt    480 cacgttctgg gtaagaatct ggagttcaac tttacgccgc attgcctgta catttggggt    540
gatcaggcta accatggtct gaaatctgct tttaagattt gccacgagat caccggttct    600
aaaggcgatt ttattgtagc agatcacacc cagatgaaca ctccaatcgg tggtggccca    660
gtgcacgtgc cggagtatca ccatatgagc tatcacgtta gctgtccaa agacgtcacg    720 gatcaccgtg ataatatgtc cctgaaagag accgtccgcg ccgtggactg ccgtaaaacc    780
tatctgtaa                                                           789
```

<210> SEQ ID NO 12
<211> LENGTH: 753
<212> TYPE: DNA
<213> ORGANISM: Artificial
<220> FEATURE:
<223> OTHER INFORMATION: R9 Peptide-YFP Fusion Protein

<400> SEQUENCE: 12

```
atgcgtcgtc gccgccgtcg ccgtcgtcgt catcatcacc accatcacgg ctcttccggt    60
gccctgctgt tccacggtaa aattccgtat gtggttgaga tggagggtaa tgttgatggc    120
catactttct ccatccgcgg caaaggttat ggcgacgcgt ctgttggtaa agtggacgca    180
caattcattt gtaccaccgg cgatgtgccg gtgccgtgga caccctggt gaccacgctg    240 acttacggtg cgcagtgctt tgctaaatac ggtccggagc tgaaagactt ctacaaatcc    300
tgcatgccgg acggctacgt gcaagagcgt accatcacct tgagggcga cggcaacttc    360 aaaacccgcg cagaggttac cttcgagaat ggttctgtgt ataaccgcgt caaactgaac    420
ggccagggct caaaaagga cggccacgtc ctgggcaaaa acctggagtt caacttcacc    480
ccgcattgtc tgtacatttg gggcgatcag gctaatcacg gtctgaaatc tgcgttcaaa    540
```

-continued

```
atctgtcacg agatcacggg ttctaaaggt gatttcatcg tcgcggacca tactcagatg    600
aacacgccga ttggcggtgg tccggtgcat gttccggagt accaccacat gtcttaccac    660
gtgaaactgt ctaaagacgt aactgaccac cgtgacaaca tgtctctgaa agaaaccgtc    720
cgtgctgtag actgccgtaa gacctatctg tga                                 753

<210> SEQ ID NO 13
<211> LENGTH: 22
<212> TYPE: PRT
<213> ORGANISM: Artificial
<220> FEATURE:
<223> OTHER INFORMATION: PEP1 peptide

<400> SEQUENCE: 13

Met Lys Glu Thr Trp Trp Glu Thr Trp Trp Thr Glu Trp Ser Gln Pro
1               5                   10                  15

Lys Lys Lys Arg Lys Val
            20

<210> SEQ ID NO 14
<211> LENGTH: 11
<212> TYPE: PRT
<213> ORGANISM: Artificial
<220> FEATURE:
<223> OTHER INFORMATION: TAT peptide

<400> SEQUENCE: 14

Tyr Gly Arg Lys Lys Arg Arg Gln Arg Arg Arg
1               5                   10
```